(12) United States Patent
Hsieh (10) Patent No.: US 12,197,273 B2
(45) Date of Patent: Jan. 14, 2025

(54) SYSTEM AND METHOD FOR DIAGNOSING SYSTEM PROBLEMS

(71) Applicant: AI point AI & Environment Co., Ltd., Taichung (TW)

(72) Inventor: Wen-Pin Hsieh, Taichung (TW)

(73) Assignee: AI point AI & Environment Co., Ltd., Taichung (TW)

( * ) Notice: Subject to any disclaimer, the term of this patent is extended or adjusted under 35 U.S.C. 154(b) by 296 days.

(21) Appl. No.: 17/561,712

(22) Filed: Dec. 24, 2021

(65) Prior Publication Data
US 2023/0205616 A1    Jun. 29, 2023

(51) Int. Cl.
*G06F 11/07* (2006.01)
(52) U.S. Cl.
CPC ........ *G06F 11/079* (2013.01); *G06F 11/0736* (2013.01)

(58) Field of Classification Search
CPC ................ G06F 11/079; G06F 11/0736
See application file for complete search history.

(56) References Cited

U.S. PATENT DOCUMENTS

| | | | | |
|---|---|---|---|---|
| 2013/0113631 | A1* | 5/2013 | Pitchford | H04W 52/0229 |
| | | | | 340/870.02 |
| 2014/0379302 | A1* | 12/2014 | Park | G05B 23/0221 |
| | | | | 702/183 |
| 2021/0283554 | A1* | 9/2021 | McMurray | A01N 25/10 |
| 2021/0356221 | A1* | 11/2021 | Blay | F28C 1/14 |
| 2022/0383038 | A1* | 12/2022 | Hines | G06N 3/045 |

* cited by examiner

*Primary Examiner* — Jigar P Patel
(74) *Attorney, Agent, or Firm* — Hannah Tien (57) ABSTRACT

The present invention provides the novel AI automatic sensor full defense system and method for determining the types of sensor problems in water quality data, which can be applied in the monitoring of the processing system.

9 Claims, 9 Drawing Sheets

SYSTEM AND METHOD FOR DIAGNOSING SYSTEM PROBLEMS

FIELD OF THE INVENTION

The present invention discloses novel AI automatic sensor system and method for determining the types of sensor problem in water quality data.

BACKGROUND OF THE INVENTION

Sensors are the most important component of internet of things (IOT) and artificial intelligence (AI) industry. However, it is usually hard to clarify whether the problems belong to system problems or sensor problems due to several inaccurate procedure involved. Inaccurate sensors even lead to the serious misjudgment of artificial intelligence prediction and decision-making system.

Another critical issue is that when the sensor sends out an alarm, the operator cannot accurately determine whether the system is faulty or the sensor is inaccurate and abnormal. The common problems of sensor included the signal offset, the gradient descent, the disconnection, the delay, the interference, no changing and poor quality warning.

Hence, the detection of the sensors should be classified accurately to raise the effectiveness in both the IOT and AI industry. In other words, establishing the system and monitoring method to categorize the types of sensor problems can benefit for the working system. Accordingly, there exists strong demand for accurate identification of the types of sensor problems.

SUMMARY OF THE INVENTION

In view of the above technical circumstances, the present invention provides a novel AI automatic sensor system for determining the types of sensor problem in water quality data, comprising: a sensor for collecting water quality data; a data correction module for exclusion the bias data and a means for categorization of the sensor problem types from receiving the said collection water quality data.

The said data correction module for exclusion the bias data was evaluated by comparing with the standard recording values. The standard recording values were collected from the commercially available standard values and would be regularly updated and re-collected.

The said means for categorization of the sensor problem types from receiving the said collection water quality data, comprising: at least one processor, which acquires one or more set of data from the said water quality data; a paired data determination module, which determines whether the said acquiring one or more set of data is paired; a drifting data determination module, which determines whether the said acquiring one or more set of data is drifting; and a $1^{st}$ data quality monitoring module, which examines the problematic condition of said one or more acquiring set of data.

The $1^{st}$ data quality monitoring module comprises missing value determination module, zero value determination module, update timing abnormality determination module and unchanged data detection module.

With the said paired data determination module, the said drifting data determination module and the said $1^{st}$ data quality monitoring module, it can be determined whether the problem is a sensor problem or not.

The present invention further comprises a $2^{nd}$ data quality monitoring module, which examines the problematic condition of said one or more acquiring set of data, comprising: sudden distribution determination module and periodic fluctuation detection module.

The present invention provides a method for determining the types of sensor problem in water quality data, comprising: (a) receiving one or more set of water quality data; (b) identifying one or more set of said receiving data is bias; (c) determining the presence or absence of bias data; (d) excluding one or more set of said receiving bias data; (e) identifying one or more set of said receiving data is paired; (f) determining the presence or absence of paring data; (g) identifying one or more set of receiving data is drifting wherein the step (f) presence of at least one paring data; (h) determining the presence or absence of drifting data; (i) identifying one or more set of receiving data presents missing value wherein the step (f) lacks of any set of said paring data; (j) determining the presence or absence of one or more set of said missing value; (k) identifying one or more set of receiving data presents zero value wherein the step (f) lacks of any set of said paring data; (l) determining the presence or absence of one or more set of said zero value; (m) identifying one or more set of receiving data presents update timing abnormality wherein the step (f) lacks of any set of said paring data; (n) determining the presence or absence of one or more set of said update timing abnormality; (o) identifying one or more set of receiving data presents unchanged value wherein the step (f) lacks of any set of said paring data; and (p) determining the presence or absence of one or more set of said unchanged value.

According to the present method, wherein the step (h) presents at least one or more set of said drifting data, or wherein the step (j) presents at least one or more set of said missing value, or wherein the step (l) presents at least one or more set of said zero value, or wherein the step (n) presents at least one or more set of said update timing abnormality, or wherein the step (p) presents at least one or more set of said unchanged value, the problems were classified as sensor alarm.

According to the present method, wherein the step (h) lacks of any set of said drifting data, the method further comprises: (i) identifying one or more set of receiving data presents missing value; (j) determining the presence or absence of one or more set of said missing value; (k) identifying one or more set of receiving data presents zero value; (l) determining the presence or absence of one or more set of said zero value; (m) identifying one or more set of receiving data presents update timing abnormality; (n) determining the presence or absence of one or more set of update timing abnormality; (o) identifying one or more set of receiving data presents unchanged value; and (p) determining the presence or absence of one or more set of said unchanged value.

According to the present method, wherein the step (j) presents at least one or more set of missing value, or wherein the step (l) presents at least one or more set of zero value, or wherein the step (n) presents at least one or more set of update timing abnormality, or wherein the step (p) presents at least one or more set of said unchanged value, the problems were classified as sensor alarm.

According to the present method, wherein the step (j) lacks of any set of said missing value, or wherein the step (l) lacks of any set of said zero value, or wherein the step (n) lacks of any set of said update timing abnormality, or wherein the step (p) lacks of any set of said unchanged value, the method further comprises: (q) identifying one or more set of receiving data presents sudden distribution; (r) determining the presence or absence of one or more set of said sudden distribution; (s) identifying one or more set of receiving data presents periodic repetition; and (t) determining the presence or absence of one or more set of said periodic repetition.

According to the present method, wherein the step (r) presents at least one or more set of sudden distribution, or wherein the step (t) presents at least one or more set of periodic repetition, the problems were classified as quality alarm.

According to the present method, wherein the step (r) lacks of any set of said sudden distribution, or wherein the step (t) lacks of any set of said periodic repetition, the problems were classified as importing model for monitoring.

DETAILED DESCRIPTION OF THE INVENTION

Hereinafter, preferred embodiments according to the present disclosure will be described in detail with reference to the accompanying drawings. The detailed description to be disclosed below with the accompanying drawings is intended to describe exemplary embodiments of the present disclosure, and is not intended to represent only embodiments in which the present disclosure may be practiced. The detailed description below includes specific details to provide a though understanding of the present disclosure. However, those skilled in the art appreciates that the present disclosure may be practiced without these specific details.

As used herein, "a," "an," "the," "at least one," and "one or more" are used interchangeably.

EXAMPLE

The examples below are non-limited and are merely representative of various aspects and features of the present invention.

The water quality data is transmitted to the AI automatic sensor full defense system through the water sampler or the sample placed in the water. Them the system determines whether the system problem is the sensor problem or the others. The AI model is well-trained independently.

Example 1: Paired Data

Figure 1:
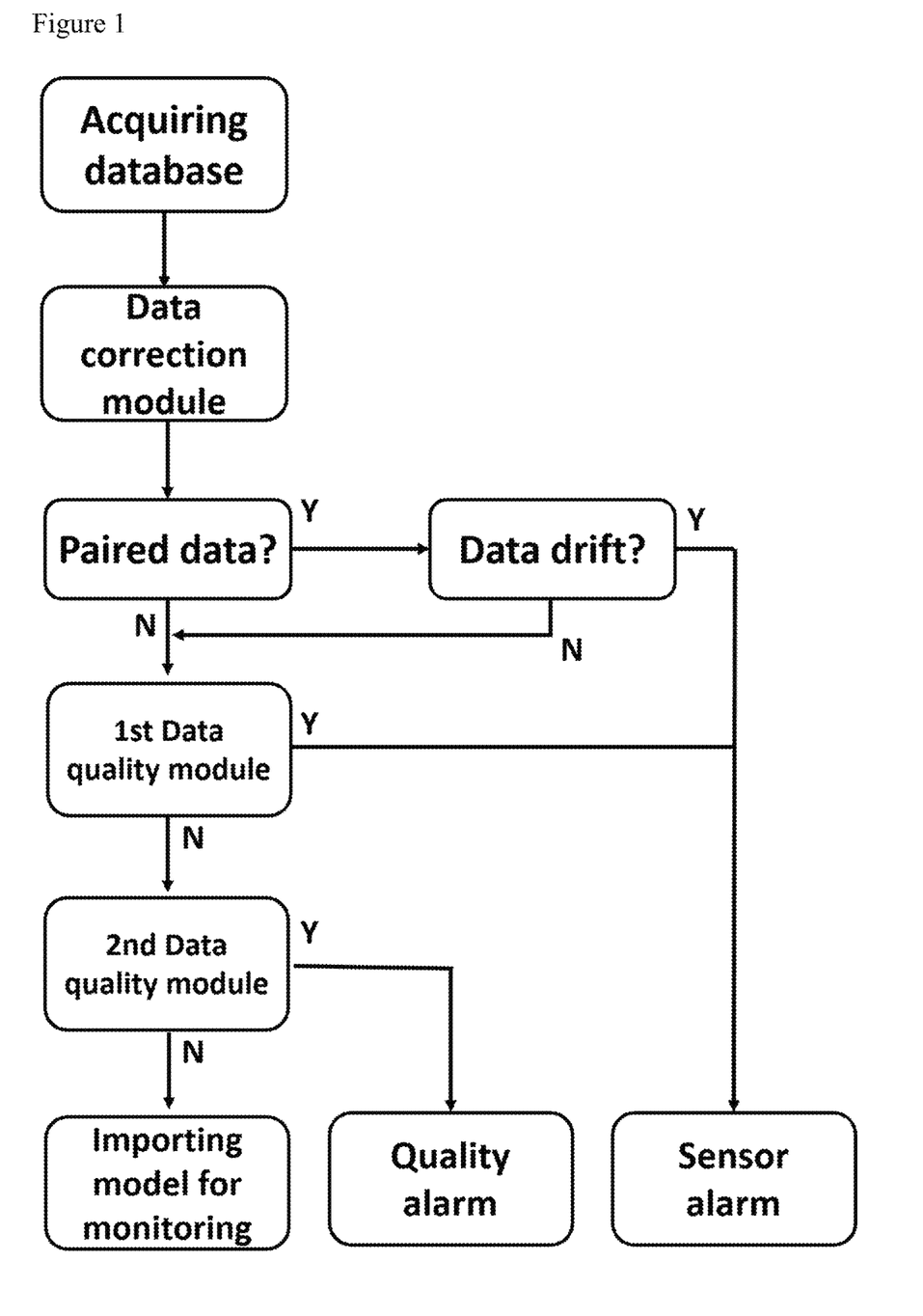
FIG. 1 is a diagram showing the disclosed system which to the method proposed in the present disclosure can be applied.
Figure 2:
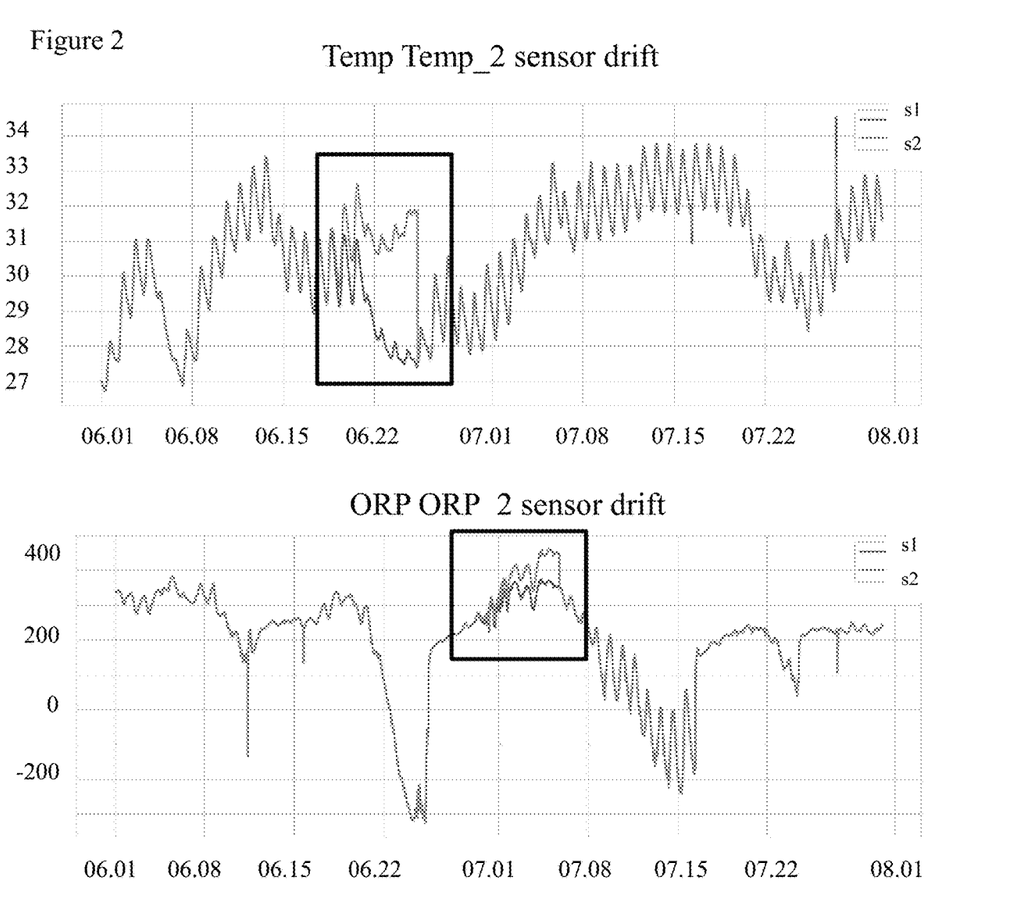
FIG. 2 illustrates an example of paired data detection of the system for determining the types of sensor problem in water quality data to which a method proposed by the present disclosure is applicable.

As shown in FIG. 2, the paired data is one embodiment classified in the sensor problem. The x-axis is the time. Take both the above and the below of FIG. 2 as an example, each scale represents 5 minutes. The y-axis of the above FIG. 2 is the temperature with degree C. unit (° C.). The y-axis of the below FIG. 2 is the oxidation-reduction potential (ORP) with mV unit.

The paired data detection is determined by the values read by the sensors at adjacent positions and are compared with the difference of their percentage between the two adjacent values. When two adjacent values are separated, it classifies as the sensor problem.

The judgements of adjacent values are on the basis of student Z test. There are two groups of sensors at the same observation point, sensor A, sensor B, respectively. After data collection, the mean values and standard deviation are calculated. Then the A test is conducted with the following assumption: H0: mean A=mean_B; H1: mean_A>mean_B or mean_A<mean_B. Performing the above values to calculate P-value at 95% confidence level. If the P value<0.025, then reject the assumption of H0 and accept the assumption of H1, indicating that the values of the two sensors are divorced.

Example 2: Drifting Data

Figure 3:
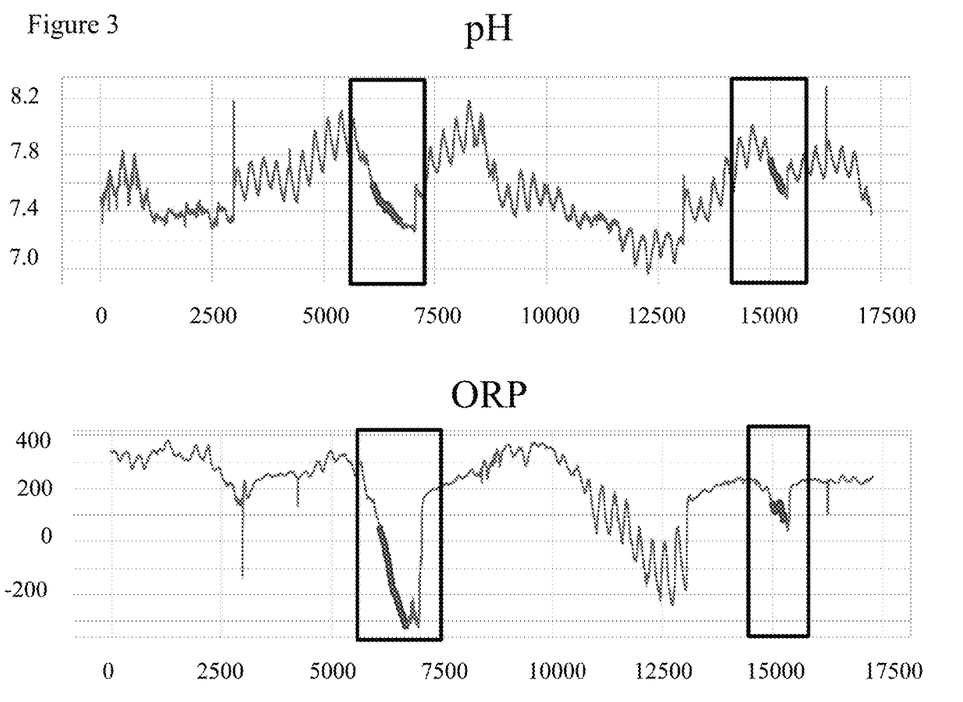
FIG. 3 illustrates an example of drifting data detection of the system for determining the types of sensor problem in water quality data to which a method proposed by the present disclosure is applicable

As shown in FIG. 3, the drifting data is one embodiment classified in the sensor problem. The x-axis is the time. Take both the above and the below of FIG. 2 as an example, each scale represents 5 minutes. The y-axis of the above FIG. 2 is the pH values. The y-axis of the below FIG. 2 is the oxidation-reduction potential (ORP) with mV unit.

The drifting data detection is determined by the algorithm to monitor the trends within the time interval of the analytic data. When the tendency continuously rises or falls in a long-term, the system judge that the water quality is abnormal. The algorithm is determined by the calculated slope. Specifically, the slope of mean_1 is calculated based on data from 0 hour to 1 hour. The slope of mean_24 is calculated based on data from 23 hours to 24 hours. If the accumulated slope in the past has the same sign (positive or negative) for more than 24 hours, it is judged as drifting data.

Example 3: Missing Value

Figure 4:
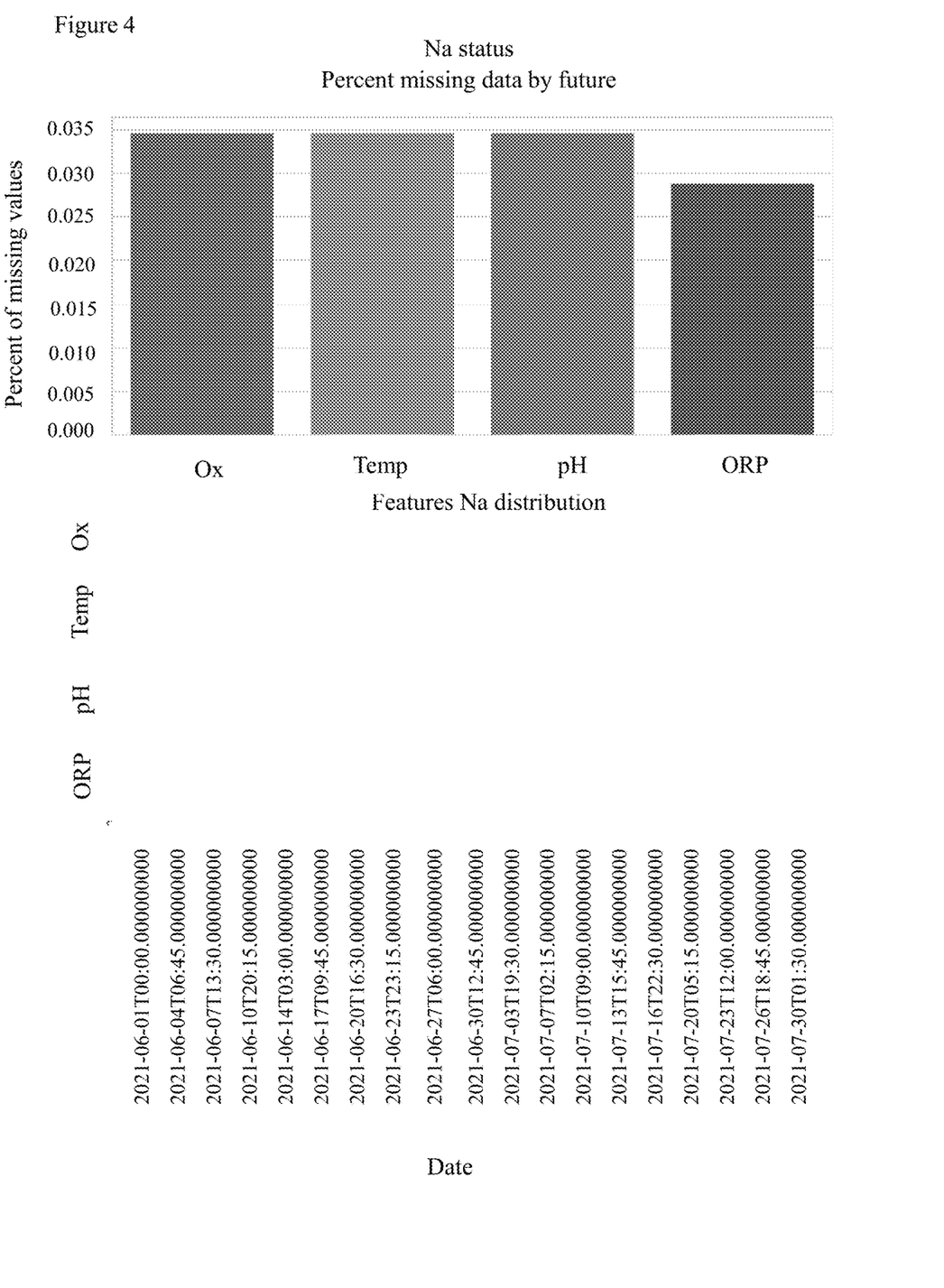
FIG. 4 illustrates an example of missing value of the system for determining the types of sensor problem in water quality data to which a method proposed by the present disclosure is applicable.

As shown in FIG. 4, the missing value is one embodiment classified in the sensor problem. The missing values is determined by the continuous collecting value. When the collecting value series are not continuous, the system judge whether there is a missing value.

Example 4: Zero Value

Figure 5:
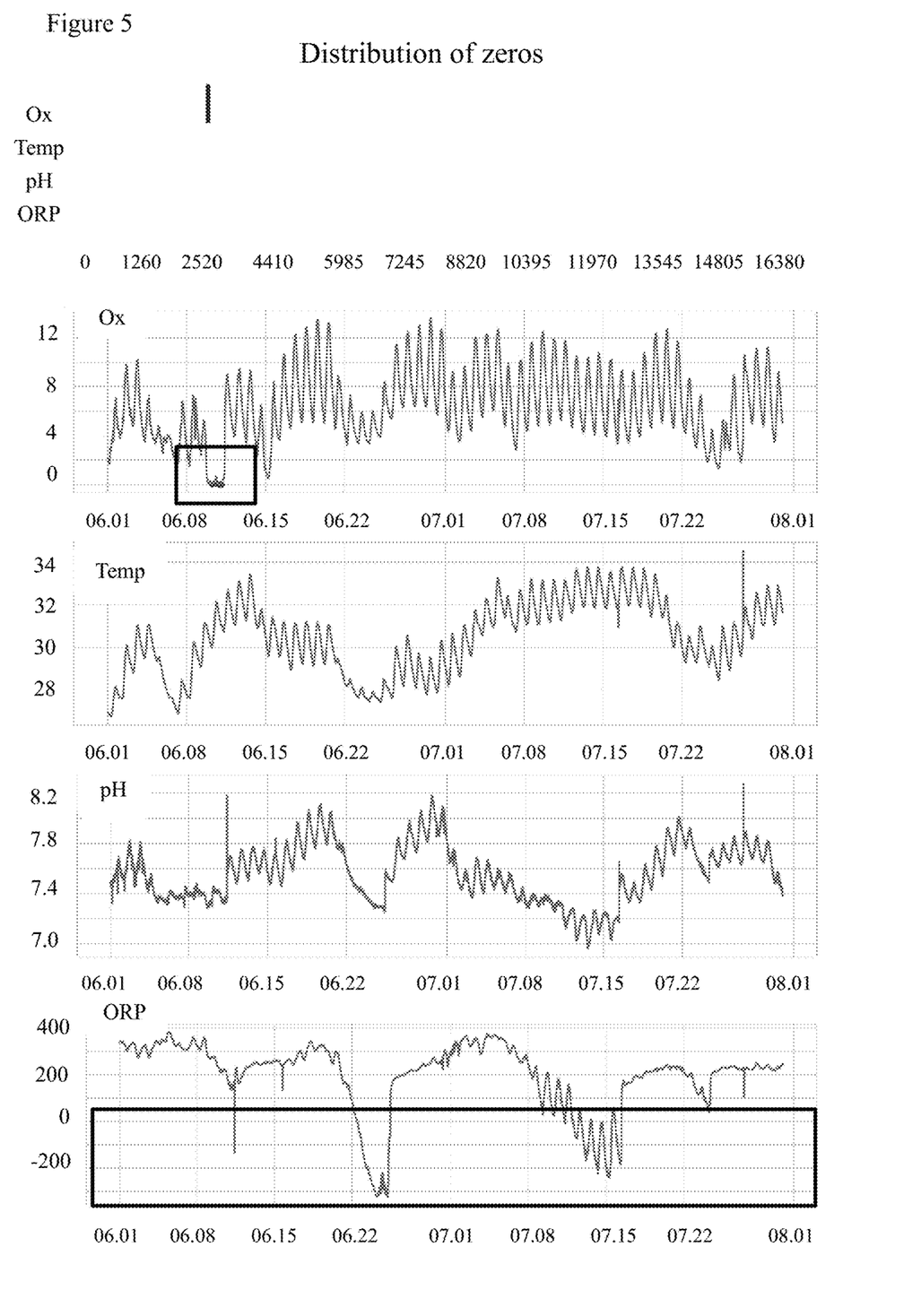
FIG. 5 illustrates an example of zero value of the system for determining the types of sensor problem in water quality data to which a method proposed by the present disclosure is applicable.

As shown in FIG. 5, the zero value is one embodiment classified in the sensor problem. The zero value is determined by the returned value of 0 or no reading, which was abnormal and made by some sensor faults.

Example 5: Update Timing Abnormality

Figure 6:
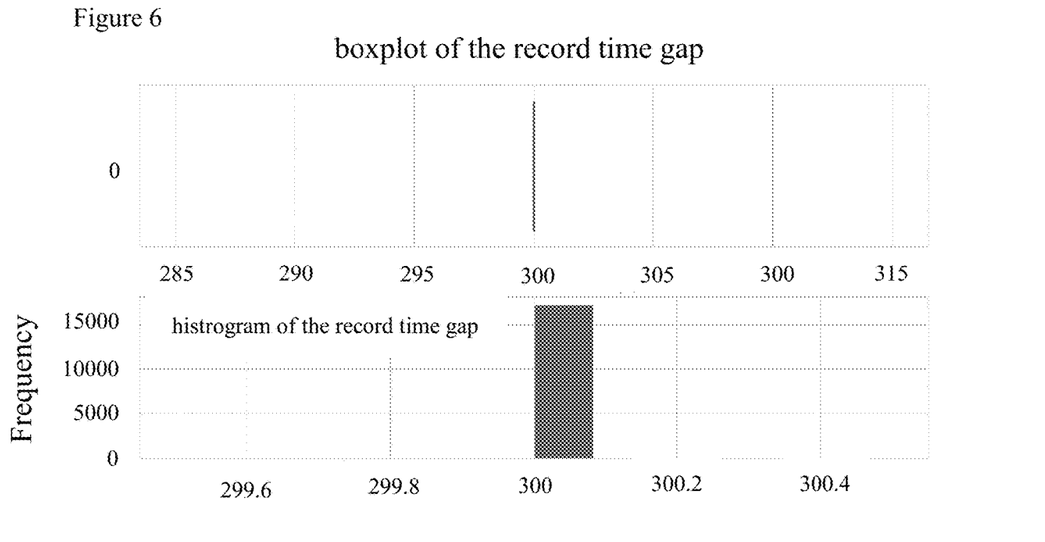
FIG. 6 illustrates an example of update timing abnormality of the system for determining the types of sensor problem in water quality data to which a method proposed by the present disclosure is applicable.

As shown in FIG. 6, the update timing abnormality is one embodiment classified in the sensor problem. The update timing abnormality is determined by the transmitter of series continuous collecting value. When the transmitter did not transmit the data at a certain time, the system judge whether there is an update timing abnormality.

Example 6: Unchanged Data Detection

Figure 7:
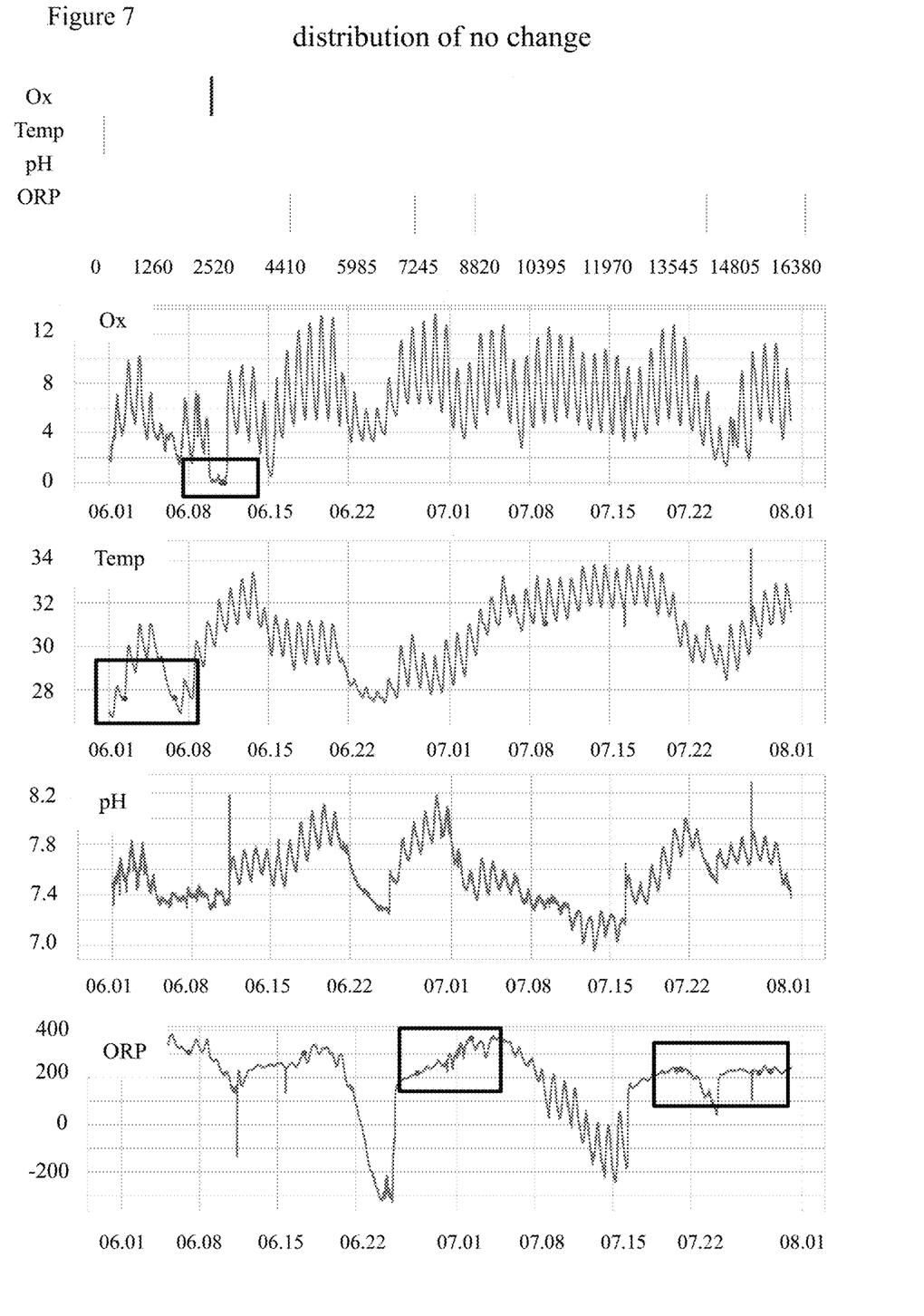
FIG. 7 illustrates an example of unchanged value of the system for determining the types of sensor problem in water quality data to which a method proposed by the present disclosure is applicable.

As shown in FIG. 7, the unchanged value is one embodiment classified in the quality alarm. When the value remains unchanged, the system judge whether there is an unchanged value.

Example 7: Sudden Distribution

Figure 8:
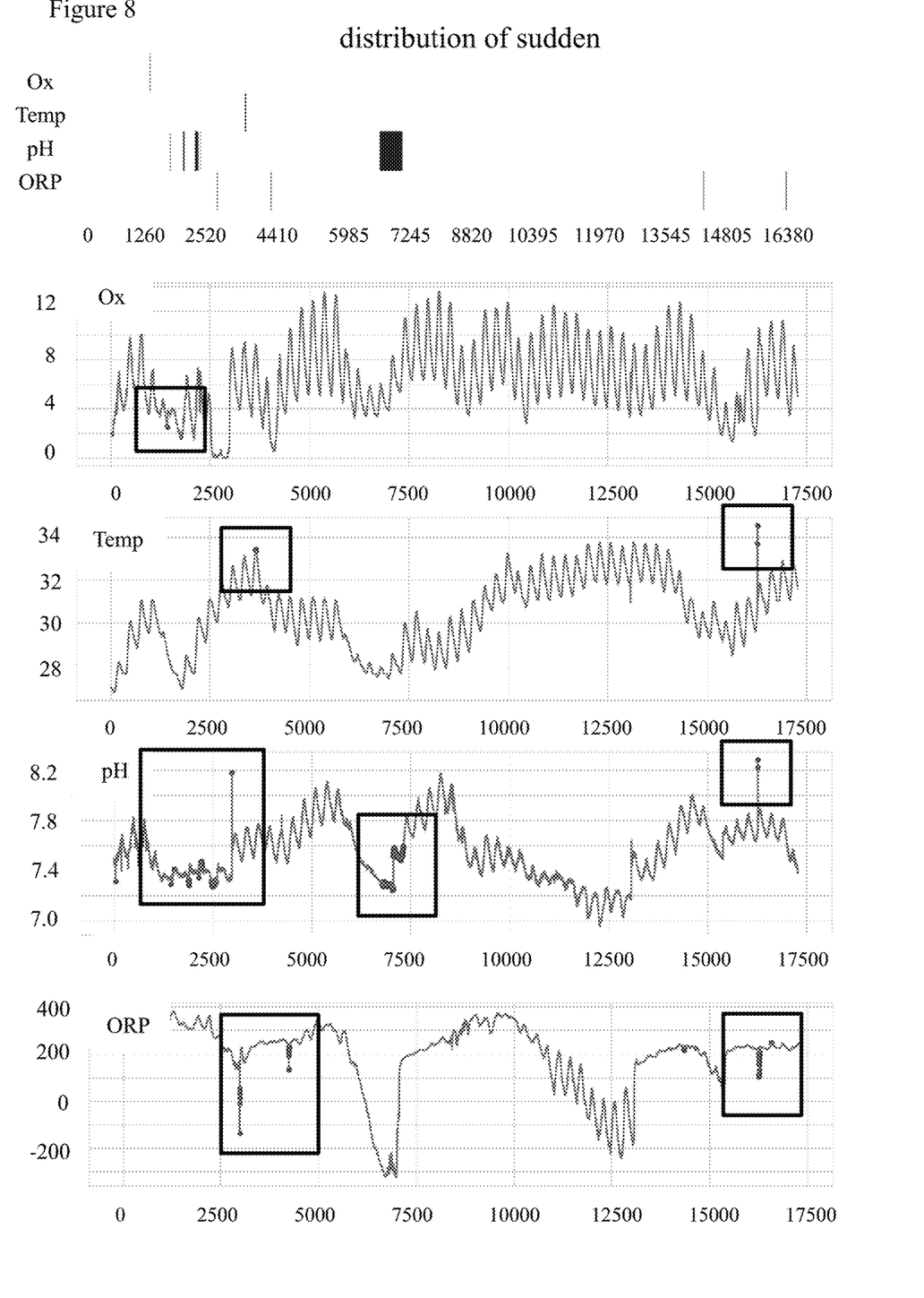
FIG. 8 illustrates an example of sudden distribution of the system for determining the types of sensor problem in water quality data to which a method proposed by the present disclosure is applicable.

As shown in FIG. 8, the zero value is one embodiment classified in the quality alarm. The sudden distribution is determined by the algorithm. When the data suddenly rises or falls to the original state, an alarm is issued.

Example 8: Periodic Fluctuation

Figure 9:
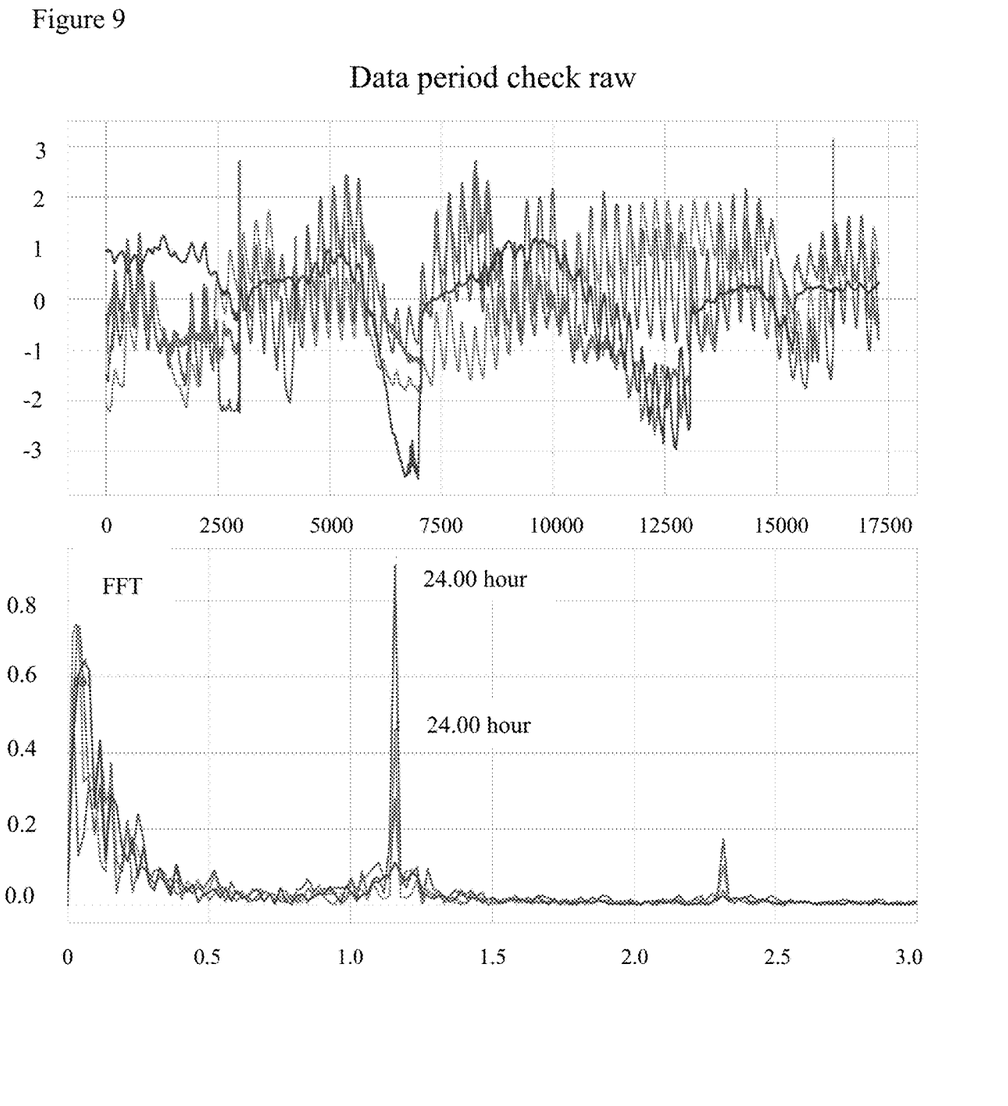
FIG. 9 illustrates an example of periodic fluctuation of the system for determining the types of sensor problem in water quality data to which a method proposed by the present disclosure is applicable.

As shown in FIG. 9, the periodic fluctuation is one embodiment classified in the quality alarm. The periodic fluctuation is determined by the environmental abnormality, such as the abnormal temperature, extreme pH value.

What is claimed is:

1. A system for determining a type of sensor problems in water quality data, comprising:
   a sensor for collecting the water quality data;
   a data correction module for exclusion of bias data via evaluation by comparing with standard recording values, in which the standard recording values are collected from commercially available standard values capable of being regularly updated and re-collected; and
   means for categorizing the type of sensor problems from receiving the said collected water quality data, including:
   at least one processor, which acquires one or more set of data from the said water quality data,
   a paired data determination module, which determines whether the said acquiring one or more set of data is paired, via determination of two adjacent values read by two sensors at adjacent positions and compared with difference of their percentage between the two adjacent values, and when the two adjacent values are separated, it classifies as a sensor problem,
   a drifting data determination module, which determines whether the said acquiring one or more set of data is drifting, wherein the drifting data detection is determined by an algorithm to monitor trends within a time interval of the analytic data, and when tendency continuously rises or falls in a long-term, the system judges that the water quality is abnormal, in which the algorithm is determined by a calculated slope, a slope of mean_1 is calculated based on data from 0 hour to 1 hour, a slope of mean_24 is calculated based on data from 23 hours to 24 hours, and if an accumulated slope in the past has a same sign (positive or negative) for more than 24 hours, it is judged as the drifting data; and
   a $1^{st}$ data quality monitoring module, which examines a problematic condition of said one or more acquiring set of data, comprising:
   a missing value determination module, in which a missing value is determined by continuous collecting values, and when the collecting values are not continuous, the system judges that there is the missing value,
   a zero value determination module, in which a zero value is determined by a returned value of 0 or no reading, which is determined abnormal and caused by a sensor fault,
   an update timing abnormality determination module, in which an update timing abnormality is determined by a transmitter for continuously collecting data, and when the transmitter does not transmit the data at a certain time, the system judges that there is an update timing abnormality, and
   an unchanged data detection module, in which an unchanged value is one embodiment classified in a quality problem, and when the value remains unchanged, the system judges there is an unchanged value,
   whereby it is determined the type of the sensor problems from the water quality data.

2. The system of claim 1, wherein the system further comprises a $2^{nd}$ data quality monitoring module, which examines a problematic condition of said one or more acquiring set of data, comprising: a sudden distribution determination module for determining whether the data suddenly rises or falls to a original state to emit an alarm; and a periodic fluctuation detection module for determining periodic fluctuation caused by environmental abnormality.

3. A method for determining a type of sensor problems in water quality data, comprising:
   (a) receiving one or more set of water quality data;
   (b) identifying if said one or more set of said receiving data is bias;
   (c) determining presence or absence of the bias data;
   (d) excluding said one or more set of said receiving bias data;
   (e) identifying if said one or more set of said receiving data is paired, via determination of two adjacent values read by two sensors at adjacent positions and compared with difference of their percentage between the two adjacent values, and when the two adjacent values are separated, it classifies as a sensor problem;
   (f) if yes, determining presence or absence of the paring data;
   (g) identifying said one or more set of receiving data is drifting, wherein the step (f) presents at least one of the paring data;
   (h) determining presence or absence of the drifting data;
   (i) identifying if said one or more set of receiving data presents a missing value, wherein the step (f) lacks of any set of said paring data;
   (j) determining presence or absence of said one or more set of said missing value;
   (k) identifying if said one or more set of receiving data presents a zero value, wherein the step (f) lacks of any set of said paring data;
   (l) determining presence or absence of said one or more set of said zero value;

(m) identifying if said one or more set of receiving data presents an update timing abnormality, wherein the step (f) lacks of any set of said paring data;

(n) determining presence or absence of said one or more set of said update timing abnormality;

(o) identifying if said one or more set of receiving data presents an unchanged value, wherein the step (f) lacks of any set of said paring data; and (p) determining presence or absence of said one or more set of said unchanged value.

4. The method of claim 3, wherein the step (h) presents at least one or more set of said drifting data, or wherein the step (j) presents at least one or more set of said missing value, or wherein the step (l) presents at least one or more set of said zero value, or wherein the step (n) presents at least one or more set of said update timing abnormality, or wherein the step (p) presents at least one or more set of said unchanged value, in which problems are classified as a sensor alarm.

5. The method of claim 3, wherein the step (h) lacks of any set of said drifting data, the method further comprising:

(i) identifying if said one or more set of receiving data presents the missing value;

(j) determining presence or absence of one or more set of said missing value;

(k) identifying if said one or more set of receiving data presents the zero value;

(l) determining presence or absence of one or more set of said zero value;

(m) identifying if said one or more set of receiving data presents said update timing abnormality;

(n) determining presence or absence of one or more set of said update timing abnormality;

(o) identifying if one or more set of receiving data presents said unchanged value; and (p) determining presence or absence of one or more set of said unchanged value.

6. The method of claim 5, wherein the step (j) presents at least one or more set of said missing value, or wherein the step (l) presents at least one or more set of said zero value, or wherein the step (n) presents at least one or more set of said update timing abnormality, or wherein the step (p) presents at least one or more set of said unchanged value, in which problems are classified as a sensor alarm.

7. The method of claim 5, wherein the step (j) lacks of any set of said missing value, or wherein the step (l) lacks of any set of said zero value, or wherein the step (n) lacks of any set of said update timing abnormality, or wherein the step (p) lacks of any set of said unchanged value, the method further comprising:

(q) identifying if the one or more set of receiving data presents a sudden distribution;

(r) determining presence or absence of one or more set of said sudden distribution;

(s) identifying if the one or more set of receiving data presents a periodic fluctuation; and (t) determining presence or absence of one or more set of said periodic fluctuation.

8. The method of claim 7, wherein the step (r) presents at least one or more set of sudden distribution, or wherein the step (t) presents at least one or more set of periodic fluctuation, in which problems are classified as a quality alarm.

9. The method of claim 7, wherein the step (r) lacks of any set of said sudden distribution, or wherein the step (t) lacks of any set of said periodic fluctuation, in which problems are classified as an importing model for monitoring.

\* \* \* \* \*